(12) United States Patent
Robertson et al.

(10) Patent No.: US 7,837,652 B2
(45) Date of Patent: Nov. 23, 2010

(54) PRESSURE INFUSION DEVICE AND PROCESS FOR MAKING A PRESSURE INFUSION DEVICE

(75) Inventors: Debra K. Robertson, Shakopee, MN (US); Andrew R. Oliverius, Eagan, MN (US)

(73) Assignee: General Electric Company, Schenectady, NY (US)

( * ) Notice: Subject to any disclaimer, the term of this patent is extended or adjusted under 35 U.S.C. 154(b) by 1199 days.

(21) Appl. No.: 11/451,192

(22) Filed: Jun. 12, 2006

(65) Prior Publication Data

US 2008/0097323 A1    Apr. 24, 2008

(51) Int. Cl.
*A61M 37/00* (2006.01)

(52) U.S. Cl. .................. 604/131; 604/142; 604/181

(58) Field of Classification Search ............. 604/80–81, 604/131–133, 140–142, 145–147, 403–404, 604/6.11, 93.01, 118, 151, 153, 181, 184–185, 604/407–408; 606/201–202; 128/888
See application file for complete search history.

(56) References Cited

U.S. PATENT DOCUMENTS

| 4,090,514 | A |   | 5/1978  | Hinck et al. |
| 4,379,453 | A |   | 4/1983  | Baron |
| 4,735,613 | A |   | 4/1988  | Bellin et al. |
| 5,053,011 | A | * | 10/1991 | Strobel et al. ............... 604/142 |
| 5,074,839 | A |   | 12/1991 | Choksi et al. |
| 7,641,647 | B2 | * | 1/2010 | Gunderson .................. 604/529 |

* cited by examiner

*Primary Examiner*—Theodore J Stigell
(74) *Attorney, Agent, or Firm*—Alan Taboada; Moser IP Law Group

(57) ABSTRACT

A pressure infusion device including a sealed bag of flexible, heat sealable material including generally opposed edge portions; a layer of substantially transparent material including generally oppose edge portions provided with a plurality of holes; the opposed edge portions of the sealed bag are folded over the opposed edge portions of the layer of substantially transparent material and are heat sealed to the sealed bag through the holes.

A process for making a pressure infusion device including the steps of providing a sealed bag of flexible, heat-sealable material having generally opposed edge portions; providing a layer of substantially transparent material including generally opposed edge portions; folding the opposed edge portions of the sealed bag over the opposed edge portions of the layer of substantially transparent material and heat sealing the folded edge portions to the sealed bag through the holes.

12 Claims, 5 Drawing Sheets

PRESSURE INFUSION DEVICE AND PROCESS FOR MAKING A PRESSURE INFUSION DEVICE

BACKGROUND OF THE INVENTION

This invention relates to a pressure infusion device for infusing a patient with a liquid, such as saline solution, blood, plasma, contained in a flexible bag, typically through the use of an I.V. needle. The infusion device applies pressure to the bag, typically made of plastic and commonly called an I.V. bag, to collapse the bag, pressurize the liquid and cause it flow into the patient.

A pressure infusion device is disclosed in U.S. Pat. No. 4,090,514 issued May 23, 1978, Howard Helmut Hinck, et al. inventors, and also is disclosed in U.S. Pat. No. 4,735,613, issued Apr. 5, 1988, Matthew E. Bellin et al. inventors; these patents are hereby incorporated herein by reference as if fully reproduced herein.

SUMMARY OF THE INVENTION

A pressure infusion device including a sealed bag of flexible, heat sealable material including generally opposed edge portions; a layer of substantially transparent material including generally oppose edge portions provided with a plurality of holes; the opposed edge portions of the sealed bag are folded over the opposed edge portions of the layer of substantially transparent material and are heat sealed to the sealed bag through the holes.

A process for making a pressure infusion device including the steps of providing a sealed bag of flexible, heat-sealable material having generally opposed edge portions; providing a layer of substantially transparent material including generally opposed edge portions; folding the opposed edge portions of the sealed bag over the opposed edge portions of the layer of substantially transparent material and heat sealing the folded edge portions to the sealed bag through the holes.

DETAILED DESCRIPTION OF THE INVENTION

Figure 1:
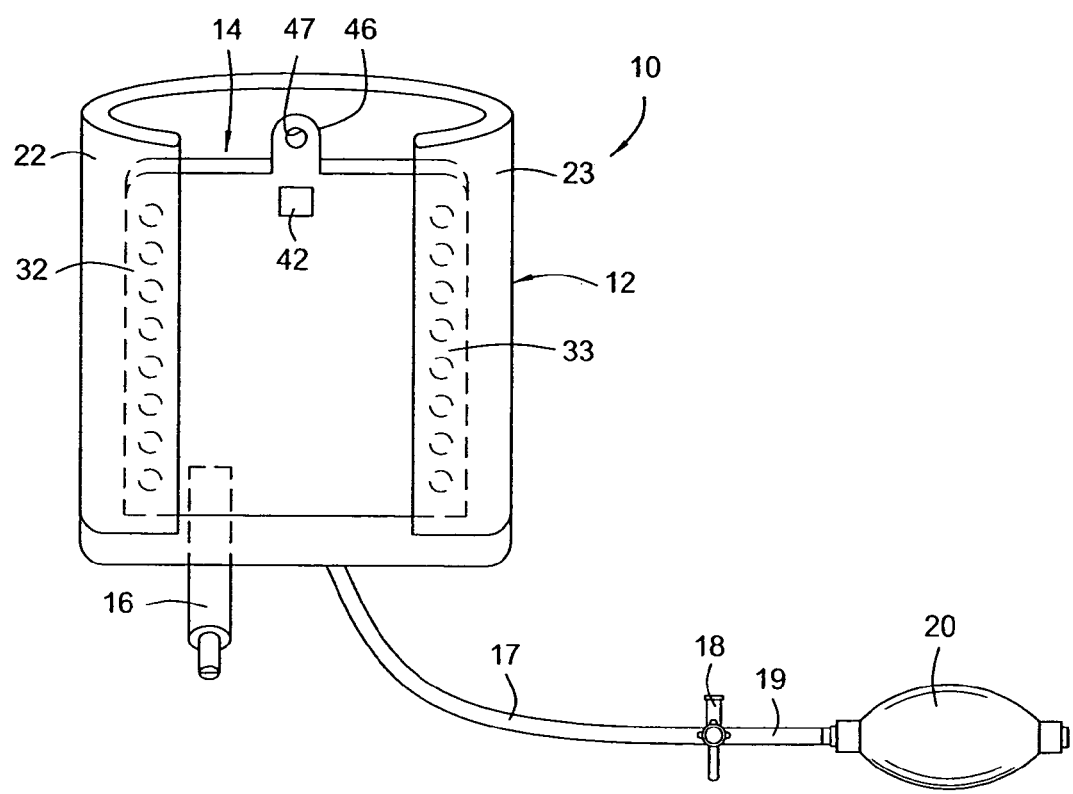
FIG. 1 shows a pressure infusion device of the present invention including a sealed bag of flexible, heat-sealable material and a layer of substantially transparent material mounted to the bag.

An embodiment of the pressure infusion device of the present invention is shown in FIG. 1 and is indicated by general numerical designation 10. The pressure infusion device 10 includes a sealed bag of flexible, heat-sealable material indicated by general numerical designation 12 and a layer of generally transparent material indicated by general numerical designation 14 mounted to the bag 12 as described below and in accordance with the process for making a pressure infusion device of the present invention.

The bag 12 is sometimes referred to in the art as a pressure bag such as the pressure bag 12 shown in FIG. 1 of the incorporated U.S. Pat. No. 4,735,613. The bag 12, FIGS. 1 and 2, may further include a pressure gauge 16, an inlet tube 17, a valve 18, a tube 19 and a squeeze bulb 20. The pressure gauge 16 may have the same structure as the pressure gauge 40 shown in FIGS. 1 and 4-7 of the incorporated U.S. Pat. No. 4,735,613 and will be understood to perform the same function as the gauge 40. Similarly, the tube 17, valve 18, tube 19 and squeeze bulb 20 of FIGS. 1 and 2 may have the same structure and perform the same functions as the tube 21, valve 22, tube 23 and bulb pump 24 shown in FIGS. 1 and 2 of the U.S. Pat. No. 4,735,613; more particularly the valve 18 of FIGS. 1 and 2 may have the same structure as the valve 22 as shown in solid outline in FIG. 1, and in cross-section in FIG. 3, of the incorporated U.S. Pat. No. 4,735,613. Alternative to the pressure gauge 16, the pressure infusion device 10 of the present invention may include the external pressure gauge 32 shown in FIGS. 1 and 2 of the incorporated U.S. Pat. No. 4,090,514.

Figure 2:
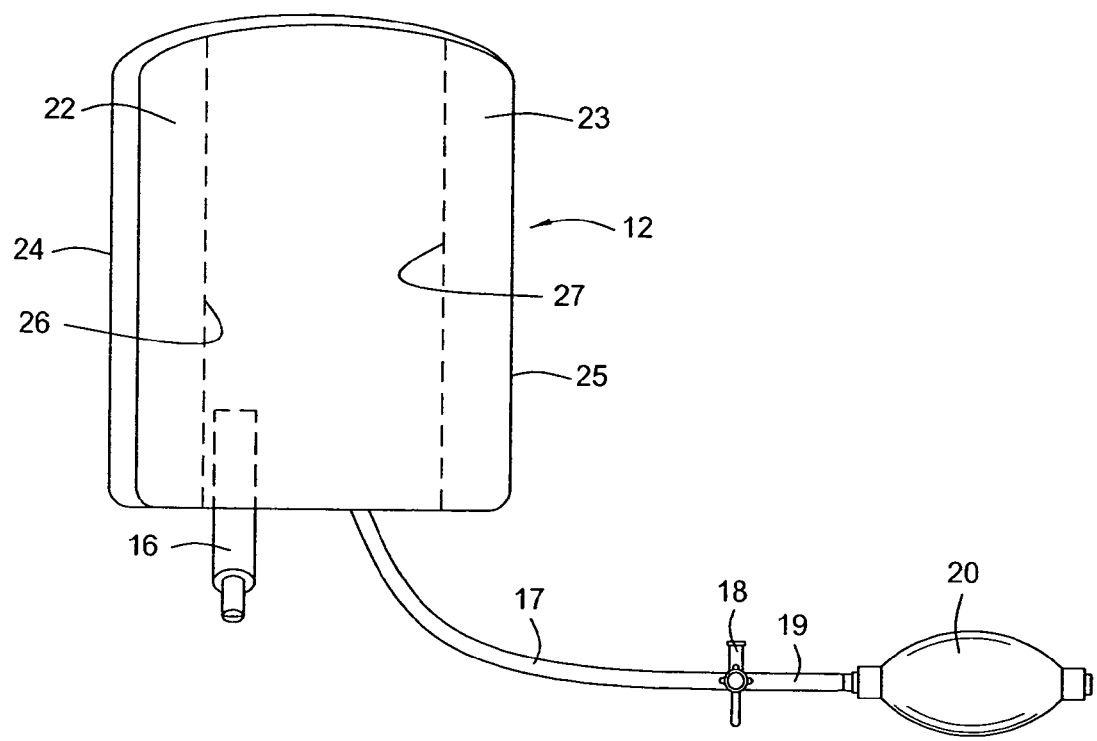
FIG. 2 shows a separate view of the sealed bag of FIG. 1.

As will be understood from FIG. 2, the bag 12 includes generally opposed edge portions 22 and 23 which are indicated diagrammatically as being the opposed edge portions bounded by the opposed edges 24 and 25 of the bag 12 and the dashed vertical lines 26 and 27. The layer of substantially transparent material 14, FIG. 3, also includes generally opposed edge portions 32 and 33 which are indicated diagrammatically as being the opposed edge portions bounded by the opposed edges 34 and 35 of the layer of substantially transparent material 14 and the vertical lines 36 and 37. The opposed edge portions 32 and 33 are provided with a plurality of holes 38 which, as shown in FIG. 3, may be disposed in two spaced apart, generally parallel, straight rows of holes.

Figure 3:
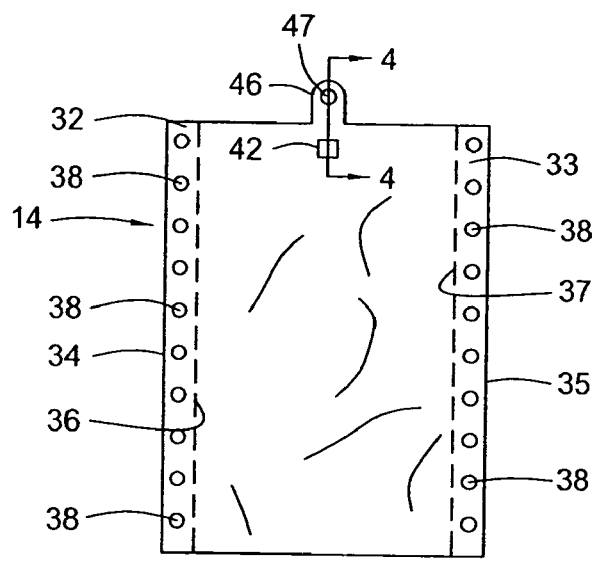
FIG. 3 shows a separate view of the layer of substantially transparent material of FIG. 1.
Figures 4, 5, 6:
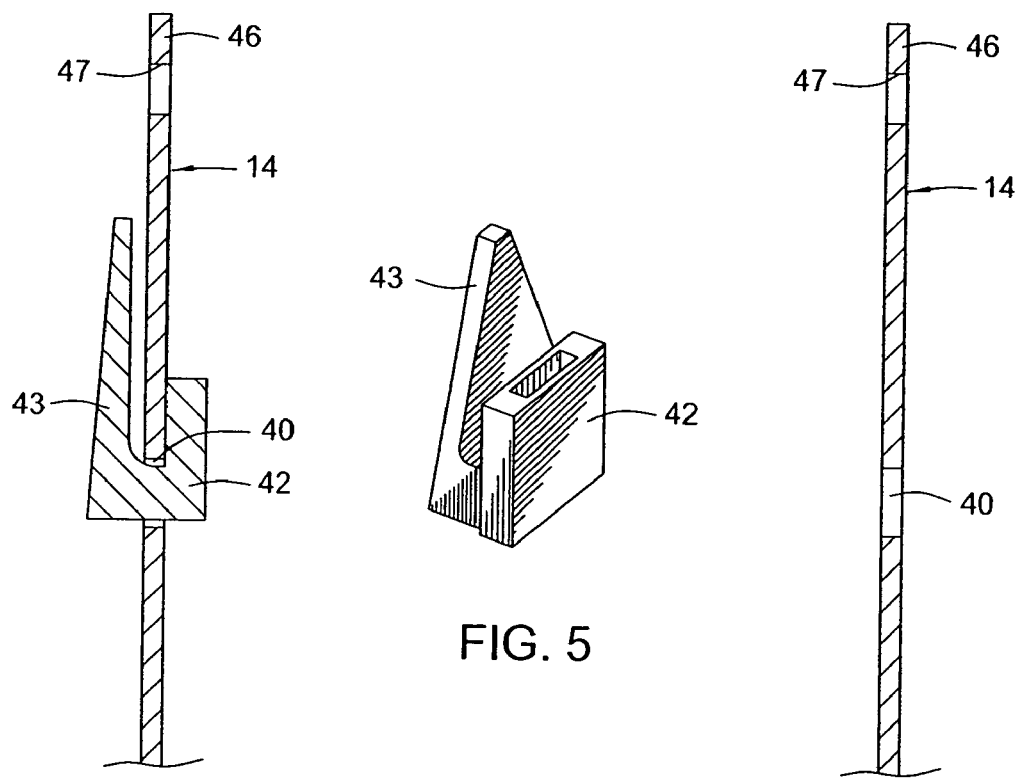
FIG. 4 is a cross-sectional view taken generally along the line 4-4 in FIG. 3 in the direction of the arrows and including a generally U-shaped mounting, or hook, member.
FIG. 5 is a view similar to FIG. 4 but with the mounting member removed.
FIG. 6 is a separate view of the mounting member in perspective.
Figure 7:
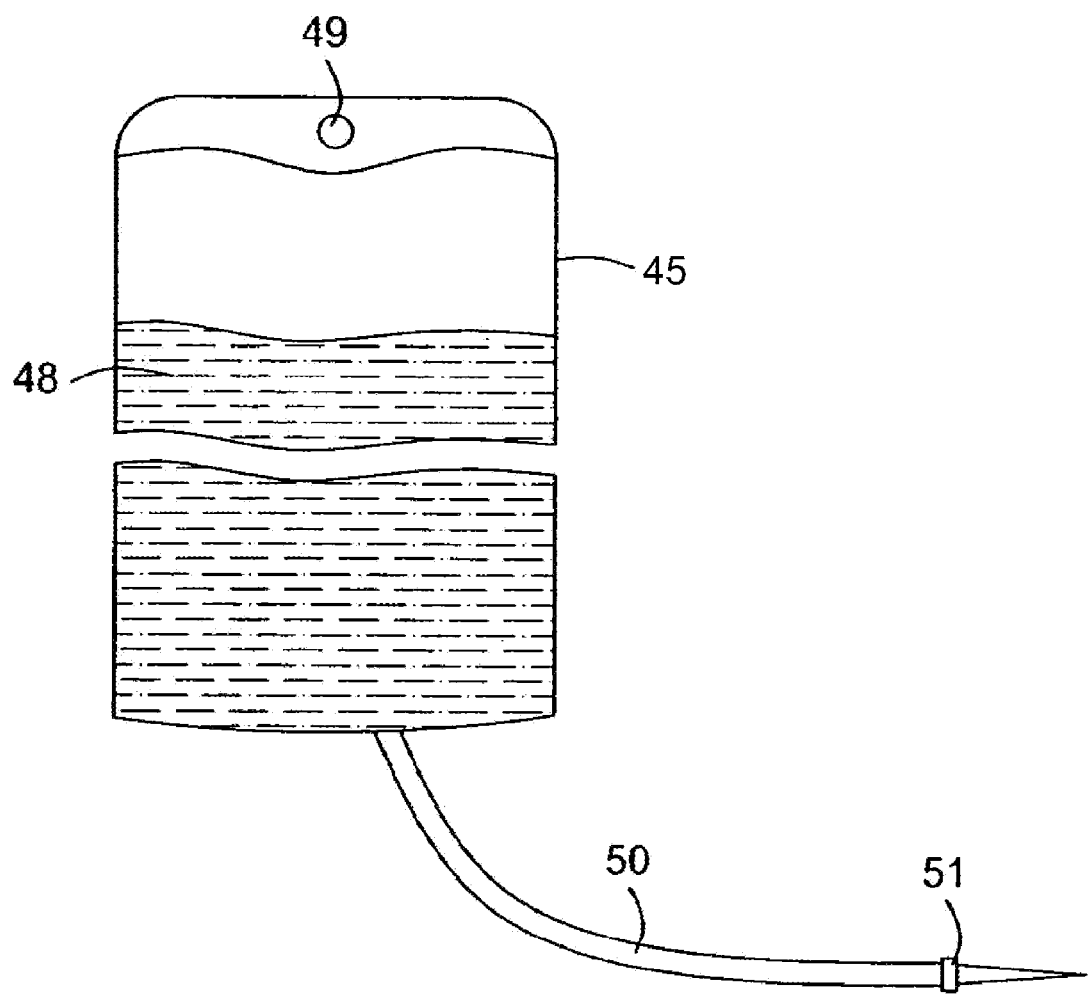
FIG. 7 is a diagrammatical front view of a flexible bag containing infusible liquid.
Figure 8:
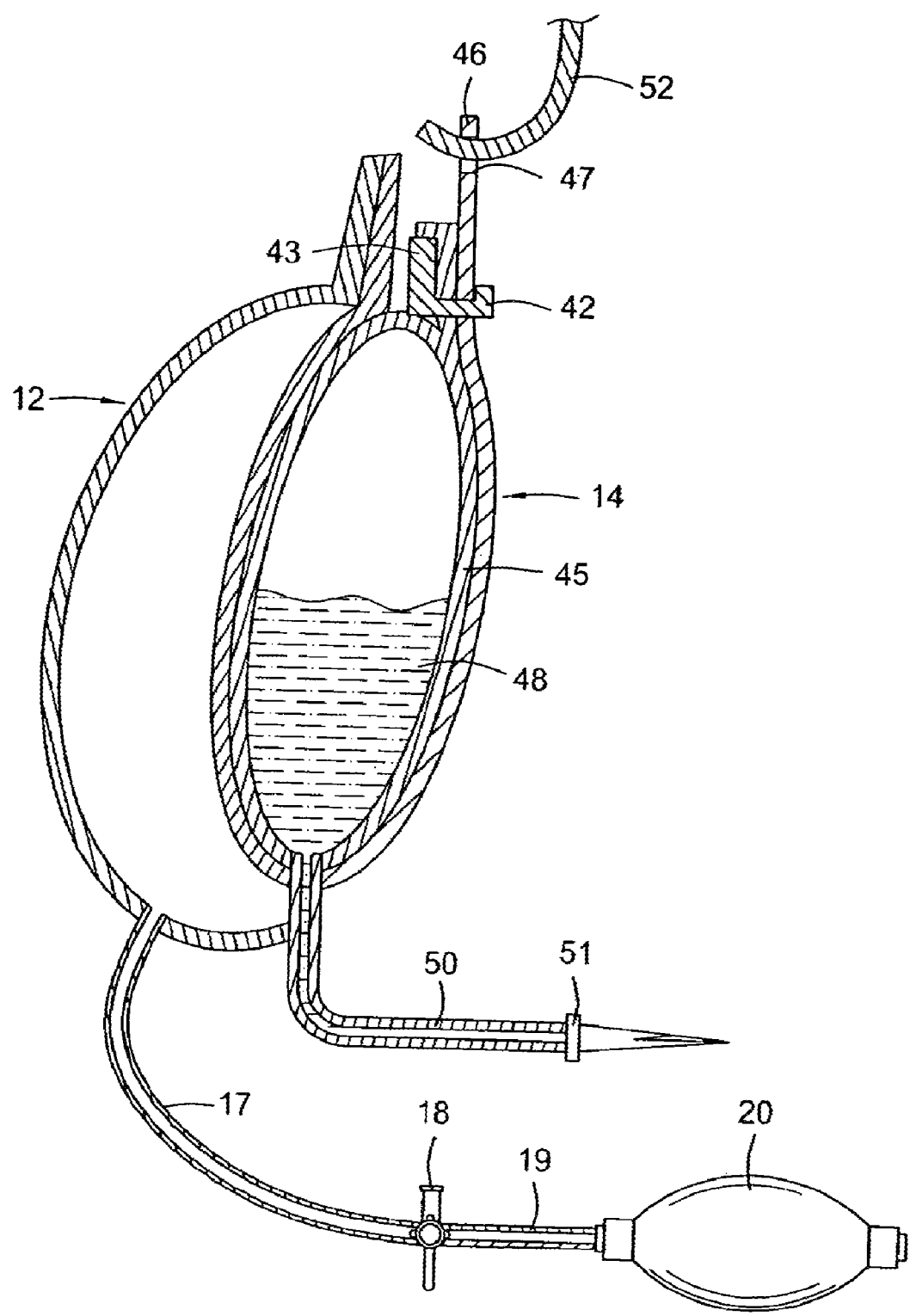
FIG. 8 is a diagrammatical cross-sectional view of the flexible bag of FIG. 7 shown mounted in the pressure infusion device of FIG. 1.

Further, the layer of substantially transparent material 14, FIGS. 3-5, may be provided with a mounting hole 40 at its upper or top portion, note particularly FIG. 5, for receiving a generally U-shaped mounting member 42, shown in FIG. 4, which includes an upwardly extending leg 43 which resides between the layer of substantially transparent material 14 and the bag 12 as shown in FIG. 8. The leg 43 is for removably mounting a flexible bag containing infusible liquid, such as the flexible bag 45 shown in FIG. 7 containing the infusible liquid 48, in the pressure diffusion device of FIG. 1, and more particularly between the layer of substantially transparent material 14 and the bag 12, of FIGS. 1 and 2, for pressurization of the bag 45 and the infusible liquid 48 to cause the pressurized liquid to flow through the tube 50 (FIGS. 7 and 8) and, for example, through the I.V. needle 51 to infuse a patient with the liquid. As will be understood from FIG. 7 the flexible bag 45 containing the infusible liquid 48 is provided at its top with a hole or opening 49 through which the leg 43 of the mounting member 42 (FIGS. 4 and 6) may be inserted to removably hook the bag 45 containing the infusible liquid 48 to the mounting member 42. Additionally, and referring further to FIG. 3, the layer of substantially transparent material 14 may be provided with an integrally formed and upwardly extending tab portion 46 provided with a hole 47 through the hook 52 (note FIG. 8) of an I.V. stand (not shown in its entirety) may be inserted to mount the pressure infusion bag 10 of the present invention as a patient is being infused.

With regard to the mounting of the layer of substantially transparent material 14 to the bag 12, and referring gain to FIG. 1, and in accordance with the process of the present invention for making a pressure infusion bag, the opposed edge portions 22 and 23 of the sealed bag of flexible, heat sealable material 12 are folded over the opposed edge portions 32 and 33 of the layer of substantially transparent material 14 to provide folded edge portions and such folded edge portions are heat sealed to the bag 12 through the holes 38 provided in layer of material 14 thereby mounting the layer of substantially transparent material 14 to the bag 12.

The process for making a pressure infusion of the present invention includes the steps of providing a sealed bag of flexible, heat sealable material having generally opposed edge portions; providing a layer of substantially transparent material including generally opposed edge portions; providing the opposed edge portions of the layer of substantially transparent material with a plurality of holes; folding the opposed edge portions of the sealed bag over the opposed edge portions of the layer of substantially transparent material to provide folded edge portions of the sealed bag; and heat sealing the folded edge portions to the sealed bag through the holes.

The sealed bag 12 of flexible, heat-sealable material may be from two layers of suitable heat-sealable material, such as for example, urethane coated nylon, with their opposed edge portions heat-sealed together. The layer of substantially transparent material 14 may be a suitable layer of at least substantially, transparent plastic film, such as for example, a layer of substantially transparent vinyl film available from the Wiman Corporation of Sauk Rapids, Minn. 56379, and sold as Product #1400; alternatively, the layer of at least substantially transparent material 14 may be a suitable commercially available layer of at least substantially transparent cast nylon.

The transparency, or at least substantially transparency, of the layer of material 14 permits, for example, a barcode or other indicia, imprinted in the flexible bag 45 containing the infusible liquid 48 (FIG. 7) to be seen and scanned through the layer of material 14.

It will be understood that many variations and modifications of the present invention may be made without departing from the spirit and scope of the present invention.

What is claimed is:

1. A pressure infusion device, comprising:
   a sealed bag of flexible, heat-sealable material including generally opposed edge portions, said sealed bag defining an interior, wherein said opposed edge portions define a portion of said sealed bag defining said interior;
   means for pressurizing said interior of said sealed bag;
   a pressure gauge in fluid communication with said interior of said sealed bag;
   a layer of substantially transparent material including generally opposed edge portions, each edge portion of said layer provided with a plurality of holes;
   said opposed edge portions of said sealed bag folded over said opposed edge portions of said layer of substantially transparent material, wherein said edge portions of said layer of substantially transparent material are heat sealed to said edge portions of said sealed bag through said holes such that said holes overlay said edge portions of said bag defining said interior, said layer of substantially transparent material thereby mounted to said sealed bag such that a space is provided between said sealed bag and said layer of substantially transparent material for receiving a flexible, indicia bearing bag containing infusible liquid; and
   said layer of substantially transparent material permitting said indicia to be seen and scanned therethrough.

2. The pressure infusion device according to claim 1, wherein said layer of substantially transparent material includes an upper portion provided with a mounting hole, wherein the mounting hole is configured to receive a generally U-shaped mounting member, the mounting member configured to removably mount said bag containing infusible liquid between said layer of substantially transparent material and said sealed bag.

3. The pressure infusion device according to claim 1 wherein said layer of substantially transparent material includes an upper edge portion provided with an integrally formed and outwardly extending tab portion provided with a hole for mounting said layer of substantially transparent material and thereby said pressure infusion device to an I.V. stand.

4. The pressure infusion device according to claim 1 wherein said sealed bag is comprised of opposed layers of heat-sealable material having opposed edge portions heat sealed together.

5. The pressure infusion device according to claim 4 wherein said opposed layers of heat-sealable material comprise opposed layers of urethane coated nylon.

6. The pressure infusion device according to claim 1 wherein said layer of substantially transparent material is a layer of substantially transparent vinyl film.

7. The pressure infusion device according to claim 1 wherein said layer of substantially transparent material is a layer of substantially transparent cast nylon.

8. The pressure infusion device according to claim 1 wherein said pressure gauge is mounted to said sealed bag and includes an internal portion residing interiorly of said sealed bag for exposure to the pressure in said sealed bag and an external portion residing exteriorly of said sealed bag.

9. The pressure infusion device according to claim 1 wherein said means for pressurizing the interior of said sealed bag includes a squeeze bulb and a length of tubing mounted to said squeeze bulb and said sealed bag and for placing said squeeze bulb in fluid communication with the interior of said sealed bag.

10. The pressure infusion device according to claim 1 wherein said plurality of holes are disposed in two spaced apart, generally parallel, straight rows of holes.

11. A pressure infusion device, comprising:
    a sealed bag of flexible, heat-sealable material including generally opposed edge portions, said sealed bag defining an interior, wherein said opposed edge portions define a portion of said sealed bag defining said interior;
    a layer of substantially transparent material including generally opposed edge portions, each edge portion of said layer provided with a plurality of holes;
    said opposed edge portions of said sealed bag folded over said opposed edge portions of said layer of substantially transparent material, wherein said edge portions of said layer of substantially transparent material are heat sealed to said edge portions of said sealed bag through said holes such that said holes overlay said edge portions of said bag defining said interior, said layer of substantially transparent material thereby mounted to said sealed bag such that a space is provided between said sealed bag and said layer of substantially transparent material for receiving a flexible, indicia bearing bag containing infusible liquid, wherein said interior is configured to be pressurized by a pressure source; and said layer of substantially transparent material permitting said indicia to be seen and scanned therethrough.

12. The pressure infusion device according to claim 11 wherein said plurality of holes are disposed in two spaced apart, substantially parallel straight rows of holes.

* * * * *

UNITED STATES PATENT AND TRADEMARK OFFICE
CERTIFICATE OF CORRECTION

| | | |
|---|---|---|
| PATENT NO. | : 7,837,652 B2 | Page 1 of 1 |
| APPLICATION NO. | : 11/451192 | |
| DATED | : November 23, 2010 | |
| INVENTOR(S) | : Robertson et al. | |

It is certified that error appears in the above-identified patent and that said Letters Patent is hereby corrected as shown below:

In column 1, line 28, delete "oppose" and substitute therefor -- opposed --;

line 31, after "transparent material and" insert -- the opposed edge portions of the sealed bag --;

line 31-32, delete "sealed bag" and substitute therefor -- opposed edge portions of the layer of substantially transparent material --;

line 41, after "edge portions" insert -- of the sealed bag --;

line 41, after "to the" delete "sealed bag" and substitute therefor -- opposed edges of the layer of substantially transparent material --.

In column 3, line 13, delete "gain" and substitute therefor -- again --;

line 21, delete "bag 12" and substitute therefor -- layer of substantially transparent material --;

line 34, after "edge portions" delete "to the sealed bag" and substitute therefor -- of the sealed bag to the layer of substantially transparent material --.

Signed and Sealed this
Nineteenth Day of April, 2011

David J. Kappos
*Director of the United States Patent and Trademark Office*